United States Patent
Tienboon

[19]
[11] Patent Number: 5,916,267
[45] Date of Patent: Jun. 29, 1999

[54] ANTERIOR SPINAL IMPLANT SYSTEM FOR VERTEBRAL BODY PROSTHESIS

[75] Inventor: Prakit Tienboon, 872 Polthep, Phatthanakarn Rd., Suan Loang Pravait, Bangkok, Thailand

[73] Assignees: Arthit Sitiso, Lakeview Terrace; Frank Bailly, San Pedro; John Wagner, Calabasas, all of Calif.; Pibul Itiravivong, Praves, Thailand; Somsak Kuptniratsaikul, Talingcharn, Thailand; Tawechai Tejapongvorachai, Bangkapi, Thailand; Prakit Tienboon, Suan Loang Pravaj, Thailand

[21] Appl. No.: 08/826,000

[22] Filed: Apr. 7, 1997

[51] Int. Cl.$^6$ .................................................. A61F 2/44
[52] U.S. Cl. .................................................. 623/17
[58] Field of Search ............................ 623/16, 17, 18; 606/61, 63

[56] References Cited

U.S. PATENT DOCUMENTS

| | | | |
|---|---|---|---|
| 5,236,460 | 8/1993 | Barber | 623/17 |
| 5,458,641 | 10/1995 | Ramirez Jimenez | 623/17 |
| 5,571,192 | 11/1996 | Schonhoffer | 623/17 |

FOREIGN PATENT DOCUMENTS 3729600  3/1989  Germany ................................ 623/17

Primary Examiner—David Isabella
Attorney, Agent, or Firm—John J. Posta, Jr.

[57] ABSTRACT

A vertebral body prosthesis is disclosed which is easily implantable intermediate the endplates of upper and lower vertebrae to replace the removed vertebral body and restore stability and normal vertebrae spacing to the spinal column while facilitating the occurrence of bony integration to fuse the aforesaid vertebrae together. A first embodiment, which may be used in the cervical spine and installed from an anterior surgical approach, is a vertebral body T-cage, which is fixed in height, and is for installation intermediate the endplates of two vertebrae located immediately above and below a removed vertebra. A second embodiment, which may be installed using a posterior surgical approach, is a fixed height vertebral body prosthesis for installation intermediate the endplates of vertebrae located immediately above and below a removed vertebra, with the device being affixed using curved mounting plates located on either the left or the right lateral side of the vertebrae. A third embodiment is a variable height vertebral body prosthesis similar to the fixed height vertebral body prosthesis, but which may be adjusted in height once it is installed in place to adjust the spacing between the vertebrae.

23 Claims, 6 Drawing Sheets

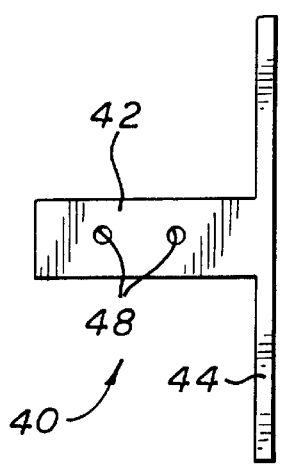
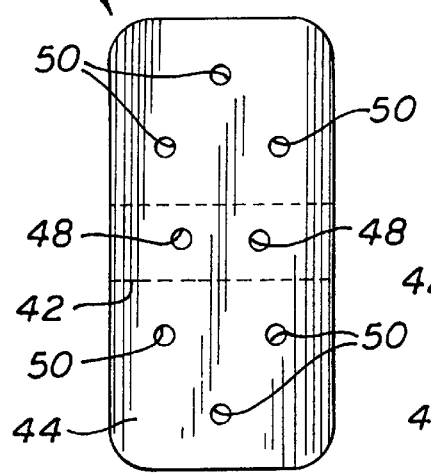
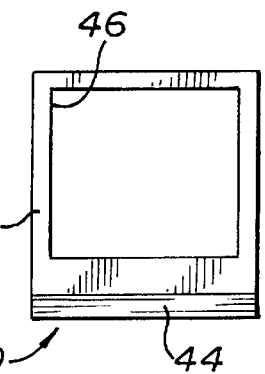
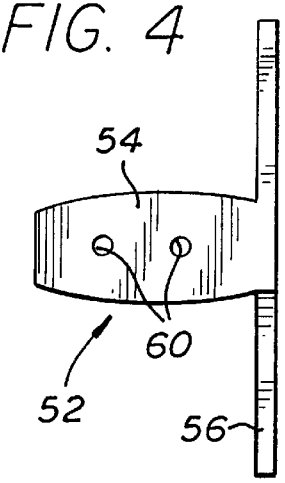
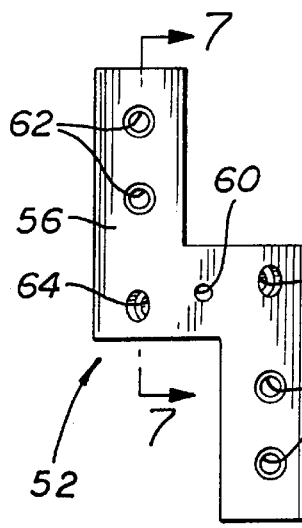
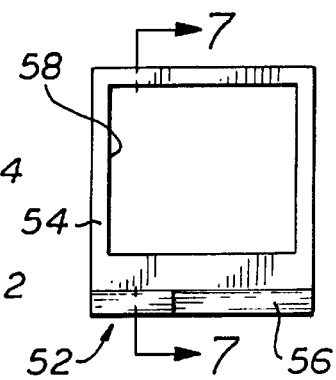
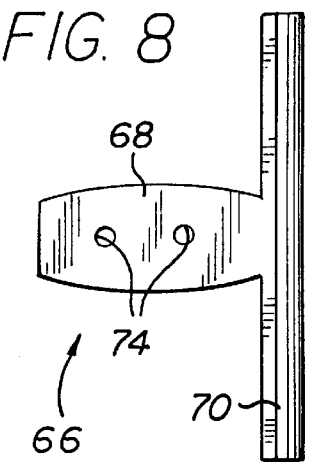
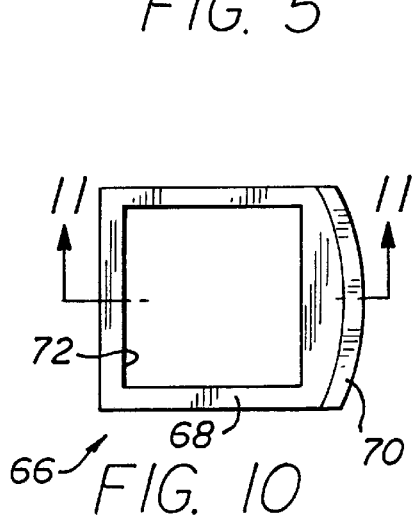
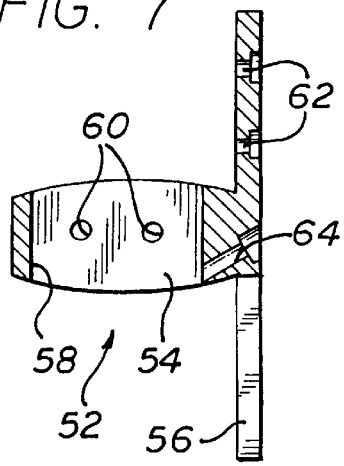

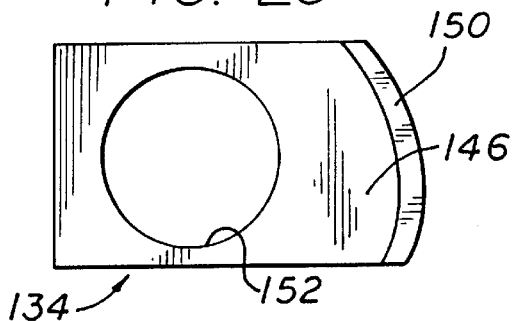
FIG. 20
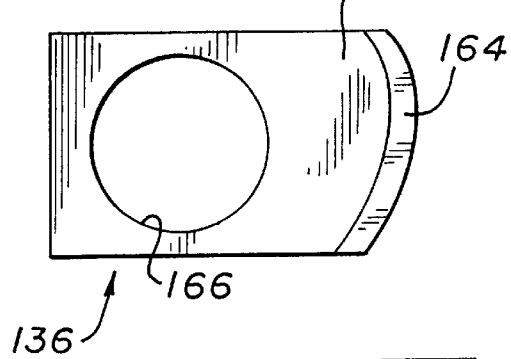
FIG. 21
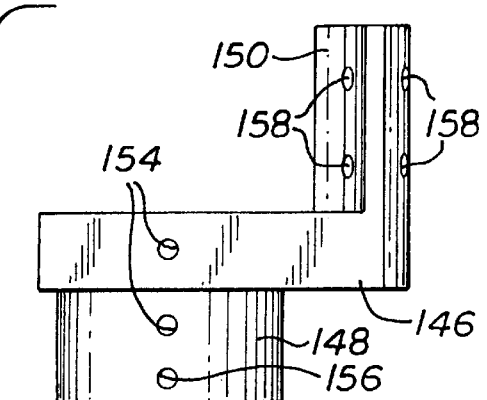
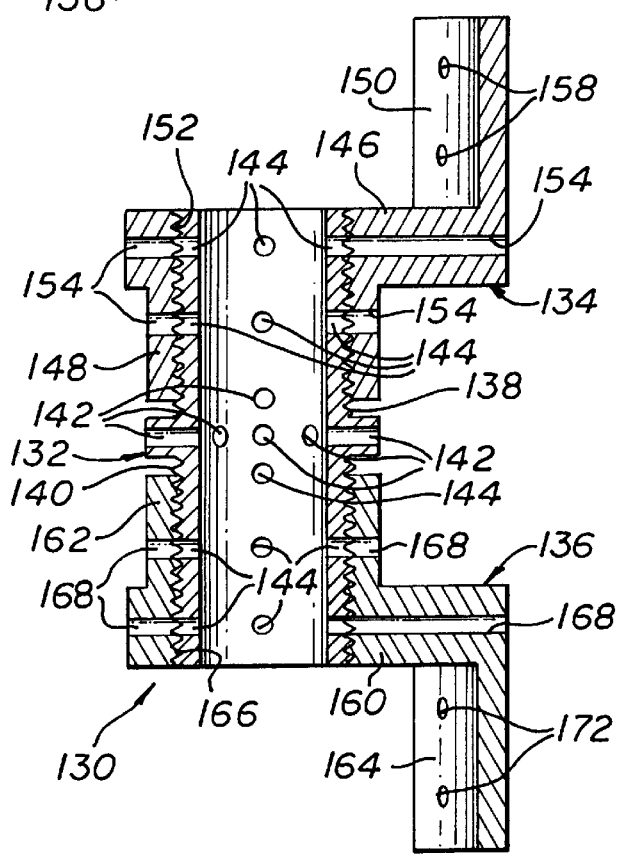
FIG. 19
FIG. 23

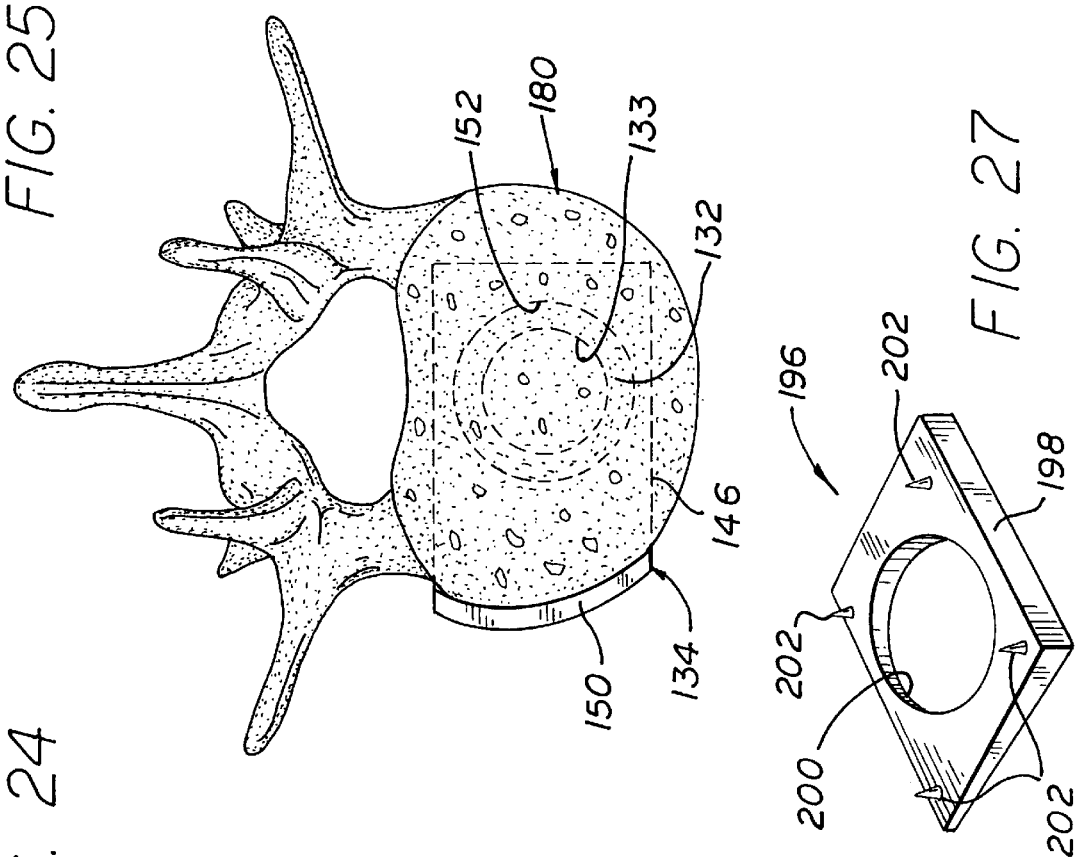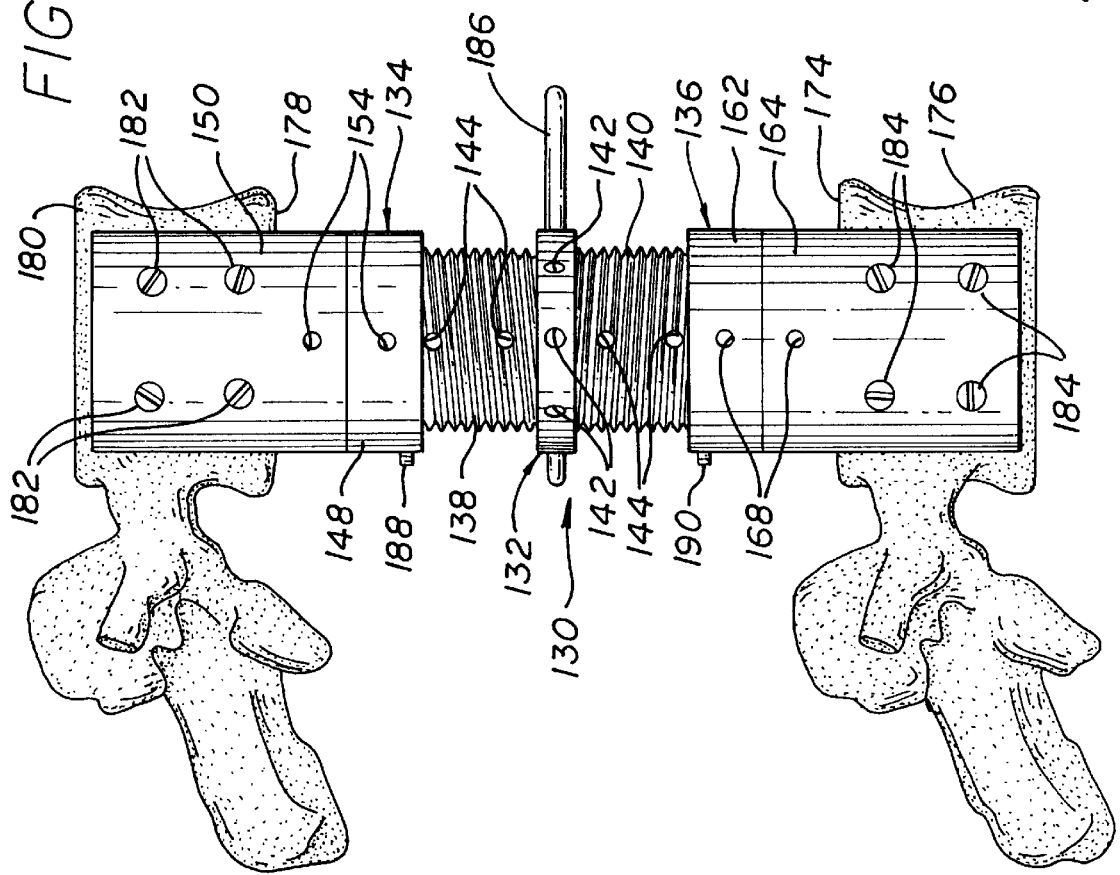

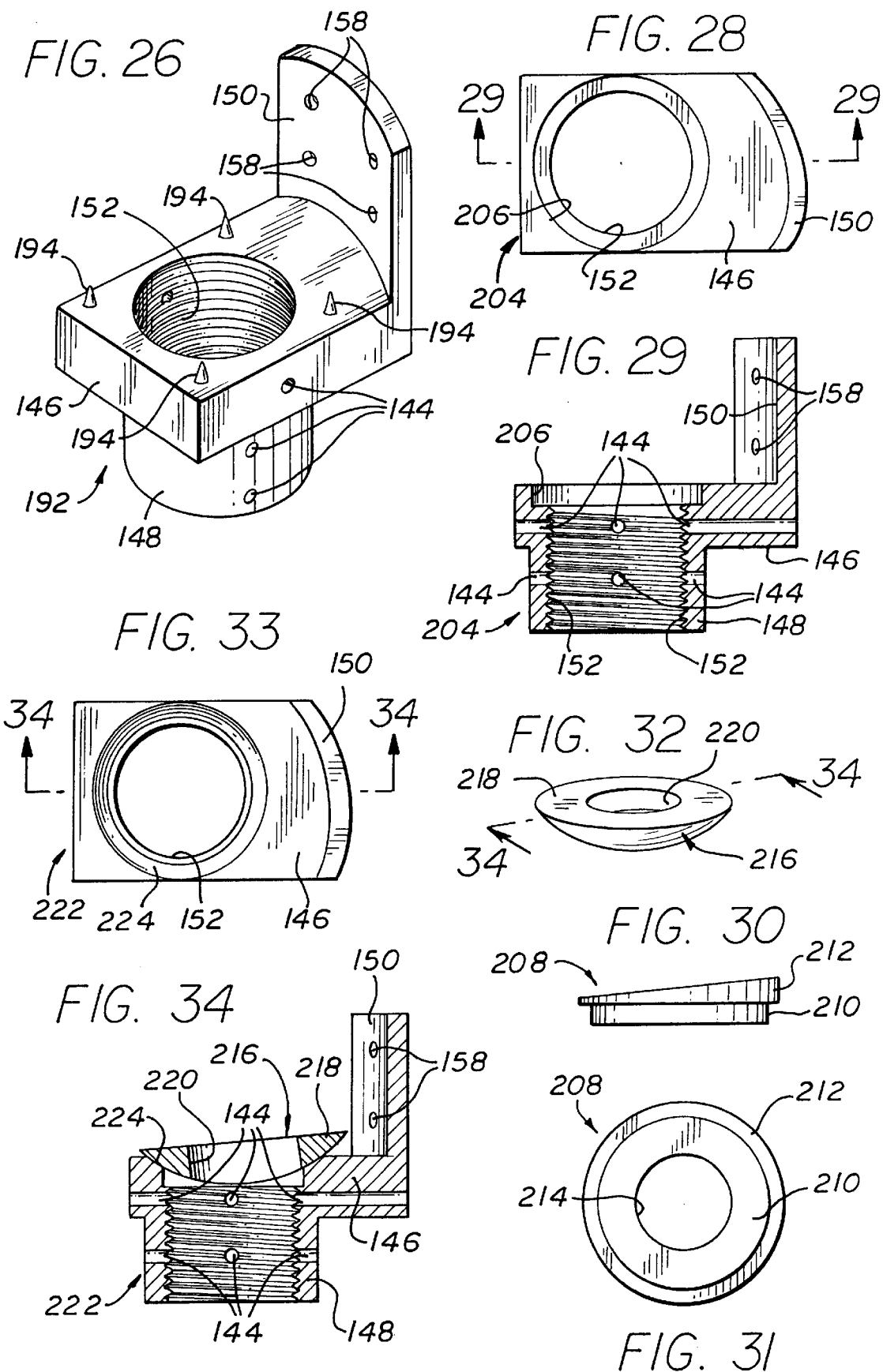

ANTERIOR SPINAL IMPLANT SYSTEM FOR VERTEBRAL BODY PROSTHESIS

BACKGROUND OF THE INVENTION

FIELD OF THE INVENTION

The present invention relates generally to prosthetic devices for the replacement of vertebrae to treat patients having spinal resection, and more particularly to an improved adjustable, easily implantable vertebral body prosthesis for insertion and permanent installation intermediate the endplates of upper and lower vertebrae to replace the removed vertebral body and restore stability and normal vertebrae spacing to the spinal column while facilitating the occurrence of bony integration to fuse the aforesaid vertebrae together.

The main structural support of the human skeleton is the spinal column, a bony column that consists of a plurality of vertebrae which are interlinked by flexible joints, spaced apart by gelatinous intervertebral disks of fibrocartilage, and held together by ligaments. Each vertebra has a roughly cylindrical body, with wing-like projections, and a bony arch. The arches, which are positioned next to one another, create a tunnel-like space which houses the spinal cord. The anterior cylindrical bodies of the vertebrae, which are spaced apart by intervertebral disks, bear most of the compressive load of the spinal column (approximately 80 percent of the total load).

When it occurs, severe back pain can be among the most relentless and debilitating afflictions occurring to individuals, often making a normal life substantially impossible for victims of such conditions. The most common causes of severe spinal ailments include primary and metastatic malignant tumors which are unresponsive to standard therapy, non-malignant tumorous vertebrae, spinal cord compression associated with paresis or paraplegia, and vertebral collapse or backbone instability. These conditions all affect the anterior cylindrical body of a vertebra, which, as mentioned above, is the primary load-carrying part of the vertebrae.

The primary objectives of surgical intervention are to preserve the neurological function of the spinal cord and to relieve the intense pain associated with such conditions. It will be appreciated particularly by those skilled in the art that any such surgical intervention will necessarily involve the resection of the spinal column and the removal of the anterior cylindrical body of the vertebra. The resulting loss of bony support destabilizes the vertebral column, and therefore requires that the excised support material be replaced either by a prosthetic implant or other filler material.

One approach has been to remove the tumorous material, and then fill the space of the resected anterior spine with methylmethacrylate or some other plastic material. This approach has been less than successful, since it is difficult to achieve proper bonding with the bony material of the vertebrae. In addition, such materials often involve an exothermic chemical reaction for the polymerization of the plastic material, which can release a significant amount of heat into the adjacent tissue. In addition, these plastic materials do not exhibit sufficient mechanical strength and stability, even when they are reinforced with metal pins or struts.

Another approach which has been utilized is to use a hollow cylindrical mesh cage which is filled with bone chips or marrow. The bone material may be bone excised from the patient's own fibula or pelvis, or, alternately, allograft material, which is bone which typically has been harvested from a deceased donor. In the case of a metastatic tumor, bone cement may be used instead of bone chips or marrow.

A spreader is used to separate the vertebrae between which the cylindrical mesh cage is to be inserted. With the distance between the vertebrae maintained by the spreader, the cylindrical mesh cage is inserted into place, with the ends of the cylindrical mesh cage (which may include teeth) bearing on the opposing endplates of the vertebrae. The spreader is then released, so that normal compressive forces of the spine acting on the anterior column may anchor the cylindrical mesh cage in place. Bone cement nay also be applied at the ends of the cylindrical mesh cage to facilitate the ends of the cylindrical mesh cage being maintained in place.

Immediate stabilization of the spine following this procedure does not occur, since it generally takes between three and six months for bony fusion to take place. In addition, if the patient is to be treated by radiation and/or chemotherapy following the surgery, in many cases the radiation and/or chemotherapy will have an adverse affect on the bone graft, preventing it from surviving and fusing the two vertebrae together. In this case, additional surgery will generally be required to establish a satisfactory degree of spinal stability.

Another technique used to stabilize the spine following the removal of the anterior column of a vertebra is the use of a plurality of metal rods which are attached by bolts or screws to the two vertebrae on either side of the removed vertebrae. This technique presents a variety of problems, particularly due to the presence of large localized forces in the areas in which the rods are attached to the vertebrae by the bolts or screws. In addition, some areas of the spine are difficult or impossible to stabilize with this technique due to the presence of sensitive tissue located adjacent to the areas in which the stabilizing rods would be used.

It is accordingly the primary objective of the present invention that it provide an improved vertebral body prosthesis which may be used following the removal of the anterior column of a vertebra to reestablish spinal stability and maintain proper spacing between the vertebrae located immediately above and below the removed vertebra. It is an objective of the vertebral body prosthesis of the present invention that it be of a design and physical configuration which may be easily installed in place intermediate the endplates of the two adjacent vertebrae via a posterior surgical approach. It is a related objective of the vertebral body prosthesis of the present invention that the implant procedure not require the use of complex tools to install and position the vertebral body prosthesis intermediate the two vertebrae.

It is an further objective of the vertebral body prosthesis of the present invention that it be implantable in a surgical procedure reducing both the trauma to the patient and the time for the surgeon to implant the device. It is also an objective of the vertebral body prosthesis of the present invention that, when installed, it will securely and permanently maintain the integrity and security of the spinal column. It is yet another objective of the vertebral body prosthesis of the present invention that it promote prompt and permanent ingrowth of bone material intermediate the vertebrae located immediately above and below the removed vertebra to facilitate permanent fusion of the spinal segment. Still further objectives of the vertebral body prosthesis of the present invention are that it be made of biocompatible material compatible with long term implant in the human body, and that it be either adjustable in length or available in different sizes and configurations to fit a wide variety of patients and different locations in the spine.

The vertebral body prosthesis of the present invention must be of a construction which is both durable and long lasting, and it must require no maintenance once it is implanted. In order to enhance the market appeal of the vertebral body prosthesis of the present invention, it should also be of a simple mechanical design and relatively inexpensive construction to thereby afford it the broadest possible market. Finally, it is also an objective that all of the aforesaid advantages and objectives of the vertebral body prosthesis of the present invention be achieved without incurring any substantial relative disadvantage.

SUMMARY OF THE INVENTION

The disadvantages and limitations of the background art discussed above are overcome by the present invention. With this invention, a vertebral body prosthesis is provided for placement intermediate the endplates of vertebrae located immediately above and below a removed vertebra. The vertebral body prosthesis of the present invention includes a vertebrae support column for placement intermediate the endplates of vertebrae. This vertebrae support column is the load-bearing component of the present invention, and it is hollow so that it may be packed with bone chips or marrow to facilitate the ingrowth and fusing of bone between the vertebrae. Screws extending through mounting brackets mounted on and extending from one side of the vertebrae support column are used to attach the vertebral body prosthesis of the present invention to the sides of the two vertebrae.

The vertebral body prosthesis of the present invention has three basic embodiments, each of which will be briefly described below. The first embodiment is a vertebral body T-cage, which is fixed in height, and which is for installation intermediate the endplates of two vertebrae located immediately above and below a removed vertebra. The T-cage may be used in the cervical spine (located in the neck), and it may be installed from an anterior surgical approach.

The T-cage consists of a vertebrae support column, which in the preferred embodiment is of square or rectangular configuration and is hollow to allow bone chips or marrow to be placed therein to facilitate bony ingrowth to fuse the two vertebrae. A plurality of blood holes are located in the sides of the vertebrae support column to provide paths for fluid communication between the interior and the exterior of the vertebrae support column. A mounting plate is located on one side of the vertebrae support column and extends both above and below the vertebrae support column. A plurality of apertures are located in both ends of the mounting plate, and screws are used to attach the mounting plate to the sides of the two vertebrae on either side of the vertebrae support column.

The mounting plate may be flat or curved to fit the sides of the vertebrae, and it may be rectangular in configuration or of a more complex shape if desired. The top surfaces of the vertebrae support column may be flat, or they may be convexly curved to better fit the endplates of the vertebrae. If desired, the thickness of the vertebrae support column may be thicker at one end thereof than it is at the other end thereof.

The second embodiment of the vertebral body prosthesis of the present invention is a fixed height vertebral body prosthesis which may be installed intermediate the endplates of vertebrae located immediately above and below a removed vertebra. The fixed height vertebral body prosthesis may be installed using a posterior surgical approach, and in the preferred embodiment has curved mounting plates for location on the left or right side of the vertebrae.

The fixed height vertebral body prosthesis comprises a hollow vertebrae support column with mounting brackets mounted at the opposing upper and lower ends thereof. Bone chips or marrow may be placed in the hollow vertebrae support column to facilitate bony ingrowth to fuse the two vertebrae. A plurality of blood holes are again located in the sides of the vertebrae support column to provide paths for fluid communication between the interior and the exterior of the vertebrae support column. The mounting brackets each include a flat, rectangular base member, with a curved mounting plate located at one side thereof. The mounting plates extend in one direction from the mounting plates.

The base member of the upper mounting block is mounted onto the upper end of the vertebrae support column, and has an aperture located therein which aperture opens into the hollow interior of the vertebrae support column. The mounting plate on the base member of the upper mounting extends upwardly therefrom. The base member of the lower mounting block is mounted onto the lower end of the vertebrae support column, and has an aperture located therein which aperture opens into the hollow interior of the vertebrae support column. The mounting plate on the base member of the lower mounting extends downwardly therefrom.

Both of the mounting plates of the fixed height vertebral body prosthesis have a plurality of apertures located therein. The base members of the upper and lower mounting blocks are located on the endplates of upper and lower vertebrae between which a vertebra has been removed. The mounting plates of the upper and lower mounting blocks may be attached to the sides of the two vertebrae using screws placed through the apertures in the mounting plates.

The third embodiment of the vertebral body prosthesis of the present invention is a variable height vertebral body prosthesis which may be installed intermediate the endplates of vertebrae located immediately above and below a removed vertebra. The variable height vertebral body prosthesis is similar to the fixed height vertebral body prosthesis in its design and in its installation, differing only in that it is made in three pieces so that its height may be adjusted once it is installed in place.

The variable height vertebral body prosthesis includes a the vertebrae support column and upper and lower mounting brackets. The vertebrae support column is hollow to allow bone chips or marrow to be placed therein to facilitate bony ingrowth to fuse the two vertebrae. The vertebrae support column has a plurality of blood holes located in the sides thereof to provide paths for fluid communication between the interior and the exterior of the vertebrae support column. The upper and lower mounting brackets each consist of a base member mounted atop a cylindrical support, with a curved mounting plate being mounted on one side of the base members of each of the upper and lower mounting brackets.

The upper and lower ends of the vertebrae support column are threaded on the outside thereof, one end being threaded with regular thread (right hand thread) and the other end being threaded with reverse thread (left hand thread). The upper and lower mounting brackets each have a threaded aperture extending through the base member and the cylindrical support. The thread in the aperture located in one of the mounting brackets is regular thread, and the thread in the aperture located in the other of the mounting brackets is reverse thread.

The mounting bracket having the regular threaded aperture is mounted onto the end of the vertebrae support column having regular thread thereon, and the mounting bracket having the reverse threaded aperture is mounted onto the end of the vertebrae support column having reverse thread thereon. The variable height vertebral body prosthesis is then installed with the base members of the upper and lower mounting blocks being located on the respective endplates of upper and lower vertebrae between which a vertebra has been removed. The mounting plates of the upper and lower mounting blocks may then be attached to the sides of the two vertebrae using screws extending through apertures located in the curved mounting plates.

Several alternate embodiments are also disclosed which are equally applicable to any of the three primary embodiment vertebral body prostheses of the present invention. Small spikes may be located on the vertebrae support column of the T-cage, or on the base members of the upper and lower mounting brackets to better retain the T-cage or the mounting brackets in position against the endplates of the vertebrae. Wedges may also be used between the base members of the upper and lower mounting brackets and the vertebrae to better fit the mounting bracket to the surface of the endplate of the vertebrae. These wedges may be either fixed in position relative to the mounting brackets, or they may be moveable with respect thereto. Several alternate embodiments of the latter configuration are disclosed herein.

It may therefore be seen that the present invention teaches an improved vertebral body prosthesis which may be used following the removal of the anterior column of a vertebra to reestablish spinal stability and maintain proper spacing between the vertebrae located immediately above and below the removed vertebra. The vertebral body prosthesis of the present invention is of a design and physical configuration which may be easily installed in place intermediate the endplates of the two adjacent vertebrae via a posterior surgical approach. The implant procedure for the vertebral body prosthesis of the present invention also does not require the use of complex tools to install and position the vertebral body prosthesis intermediate the two vertebrae.

The vertebral body prosthesis of the present invention is implantable in a surgical procedure featuring both reduced implant trauma to the patient and reduced time required for the surgeon to implant the device. When the vertebral body prosthesis of the present invention is installed in place intermediate the vertebrae located immediately above and below the removed vertebra, it will securely and permanently maintain the integrity and security of the spinal column. The vertebral body prosthesis of the present invention promotes prompt and permanent ingrowth of bone material intermediate the vertebrae located immediately above and below the removed vertebra to facilitate permanent fusion of the spinal segment. The vertebral body prosthesis of the present invention is made of biocompatible material compatible with long term implant in the human body, and it may be either adjustable in length or made in different sizes and configurations to fit a wide variety of patients and different locations in the spine.

The vertebral body prosthesis of the present invention is of a construction which is both durable and long lasting, and it requires no maintenance once it is implanted. The vertebral body prosthesis of the present invention is also of a simple mechanical design and relatively inexpensive construction to enhance its market appeal and thereby afford it the broadest possible market. Finally, all of the aforesaid advantages and objectives of the vertebral body prosthesis of the present invention are achieved without incurring any substantial relative disadvantage.

DESCRIPTION OF THE DRAWINGS

These and other advantages of the present invention are best understood with reference to the drawings, in which:

FIG. 1 is a side plan view of a vertebral body T-cage constructed according to the teachings of the present invention for installation intermediate the endplates of vertebrae located immediately above and below a removed vertebra, showing a vertebrae support column having a mounting plate attached to the side thereof, and also showing two blood holes extending through the vertebrae support column;

FIG. 2 is a back plan view of the vertebral body T-cage illustrated in FIG. 1, showing a plurality of apertures through which mounting screws may be inserted to retain the vertebral body T-cage in place;

FIG. 3 is a top plan view of the vertebral body T-cage illustrated in FIGS. 1 and 2, showing that the vertebrae support column has a square configuration and is hollow;

FIG. 4 is a side plan view of an alternate embodiment vertebral body T-cage, showing the vertebrae support column with upper and lower edges which are curved in a convex manner;

FIG. 5 is a back plan view of the vertebral body T-cage illustrated in FIG. 4, showing the mounting plate to consist of two opposed L-shaped segments having a common base leg;

FIG. 6 is a top plan view of the vertebral body T-cage illustrated in FIGS. 4 and 5, showing the square configuration of the hollow vertebrae support column;

FIG. 7 is a cross-sectional view of the vertebral body T-cage illustrated in FIGS. 4 through 6, showing the angle of one of the apertures through which a mounting screw may be inserted to retain the vertebral body T-cage in place;

FIG. 8 is a side plan view of an alternate embodiment vertebral body T-cage having a curved mounting plate;

FIG. 10 is a top plan view of the vertebral body T-cage illustrated in FIGS. 8 and 9, showing the square configuration of the hollow vertebrae support column;

FIG. 19 is an exploded side view of a variable height vertebral body prosthesis constructed according to the teachings of the present invention for right side installation intermediate the endplates of vertebrae located immediately above and below a removed vertebra, showing top and bottom mounting brackets for respective installation onto threaded top and bottom ends of a vertebrae support column;

FIG. 20 is a top plan view of the top mounting bracket for installation on the threaded top end of the vertebrae support column of the vertebral body prosthesis illustrated in FIG. 19, showing the hollow threaded interior thereof and the configuration of a curved side mounting plate located thereon;

FIG. 21 is a bottom plan view of the bottom mounting bracket for installation on the threaded bottom end of the vertebrae support column of the vertebral body prosthesis illustrated in FIG. 19, showing the hollow threaded interior thereof and the configuration of a curved side mounting plate located thereon;

FIG. 23 is a cross-sectional view of the vertebral body prosthesis illustrated in FIGS. 19 through 22, showing the installation of the top and bottom mounting brackets respectively onto the threaded top and bottom ends of the vertebrae support column;

FIG. 24 is a right side view of the vertebral body prosthesis illustrated in FIGS. 19 through 23 installed between upper and lower vertebra respectively located immediately above and below a removed vertebra, showing a handle inserted into apertures located at the midpoint of the vertebrae support column and used to adjust the height of the vertebral body prosthesis;

FIG. 25 is a top side (superior) plan view of the upper vertebra showing the vertebral body prosthesis illustrated in FIG. 24 located under the inferior endplate of the upper vertebra;

FIG. 26 is a perspective view of an alternate embodiment top mounting bracket having a plurality of small spikes located thereon to secure the top mounting bracket in place under the inferior endplate of an upper vertebra;

FIG. 27 is a perspective view of a wedge-shaped spacer for use intermediate a mounting bracket and the endplate of a vertebrae to better fit the mounting bracket to the surface of the endplate of the vertebra;

FIG. 28 is a top plan view of an alternate embodiment top mounting bracket having an annular recess located in the top surface thereof around the hollow threaded interior thereof;

FIG. 29 is a cross-sectional view of the top mounting bracket illustrated in FIG. 28, showing the depth of the annular recess located in the top surface thereof;

FIG. 30 is a side view of a rotatable wedge spacer for installation in the annular recess located in the top surface of the top mounting bracket illustrated in FIGS. 28 and 29;

FIG. 31 is a bottom plan view of the rotatable wedge spacer illustrated in FIG. 30, showing a centrally-located aperture extending therethrough;

FIG. 32 is a perspective view of a convex segment of a sphere having a centrally-located aperture extending therethrough;

FIG. 33 is a top plan view of another alternate embodiment top mounting bracket having a concave recess located in the top surface thereof around the hollow threaded interior thereof; and FIG. 34 is a cross-sectional view of the top mounting bracket illustrated in FIG. 33, showing the convex segment illustrated in FIG. 32 located in and extending above the concave recess located in the top surface of the top mounting bracket to form a wedge on the top surface of the top mounting bracket.

DETAILED DESCRIPTION OF THE PREFERRED EMBODIMENT

Figure 9:
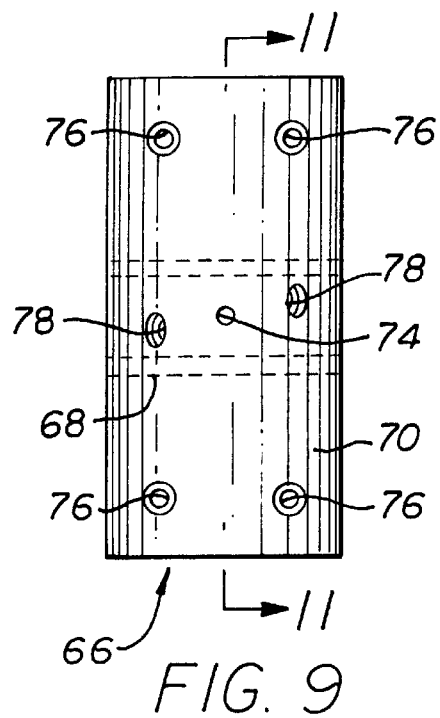
FIG. 9 is a back plan view of the vertebral body T-cage illustrated in FIG. 8.

The preferred embodiment of the vertebral body prosthesis of the present invention includes three basic embodiments, each of which will be described in this detailed description. The first of these embodiments is a vertebral body T-cage, which is fixed in height, and is for installation intermediate the endplates of two vertebrae located immediately above and below a removed vertebra. The T-cage, which may be used in the cervical spine (located in the neck) and which may be installed from an anterior surgical approach, is illustrated in and described in conjunction with FIGS. 1 through 13.

The second embodiment is a fixed height vertebral body prosthesis for installation intermediate the endplates of vertebrae located immediately above and below a removed vertebra. The fixed height vertebral body prosthesis may be installed using a posterior surgical approach, and has curved mounting plates located on the left or right side of the vertebrae. It is illustrated in and described in conjunction with FIGS. 14 through 18. The third embodiment is a variable height vertebral body prosthesis, also for installation intermediate the endplates of vertebrae located immediately above and below a removed vertebra. The variable height vertebral body prosthesis is similar to the fixed height vertebral body prosthesis in design and in its installation, differing only in that its height may be adjusted once it is installed in place. It is illustrated in and described in conjunction with FIGS. 19 through 25.

Referring first to FIGS. 1 through 3, a vertebral body T-cage 40 is illustrated which essentially consists of a vertebrae support column 42 having a flat rectangular mounting plate 44 attached to the side thereof. The side of the vertebrae support column 42 is attached to the mounting plate 44 at the midpoint of the mounting plate 44, thereby forming a T in which the vertebrae support column 42 is the base of the T and the mounting plate 44 is the top-mounted cross member of the T. The vertebrae support column 42 is square in cross-section, as illustrated in FIG. 3, and is hollow, having a square aperture 46 extending vertically therethrough. In addition, the vertebrae support column 42 is flat on both its top and its bottom, as best illustrated in FIGS. 1 and 2.

Note that the vertebrae support column 42 has a plurality of blood holes 48 extending through the lateral and anterior sides (and, although not shown in the figures, the posterior side) thereof (and thus through the mounting plate 44 as well). The blood holes 48 define a plurality of paths of fluid communication between the square aperture 46 extending through the vertebrae support column 42 and the exterior of the vertebrae support column 42 on the lateral, anterior, and posterior sides thereof.

Referring now particularly to FIG. 2, a plurality of apertures 50 extend through the mounting plate 44 both above and below its point of connection to the vertebrae support column 42. The apertures 50 are arranged and configured to have mounting screws (not illustrated in FIG. 2) inserted therethrough to retain the vertebral body T-cage 40 in place intermediate two vertebrae (also not illustrated in FIG. 2). The screws extending through the apertures 50 located above the point of connection of the mounting plate 44 to the vertebrae support column 42 will be screwed into the upper vertebra, while the screws extending through the apertures 50 located below the point of connection of the mounting plate 44 to the vertebrae support column 42 will be screwed into the lower vertebra.

Referring next to FIGS. 4 through 7, an alternate embodiment vertebral body T-cage 52 is illustrated which essentially consists of a vertebrae support column 54 having a flat mounting plate 56 attached to the side thereof. The side of the vertebrae support column 54 is attached to the mounting plate 56 at the midpoint of the mounting plate 56. The vertebrae support column 54 is square in cross-section, as illustrated in FIG. 6, and is hollow, having a square aperture 58 extending vertically therethrough. In addition, the lateral sides of the vertebrae support column 54 are convex curves on both the top and bottom of the vertebrae support column 54, as best illustrated in FIGS. 4 and 7. Note also that the height of the vertebrae support column 54 is greater at the anterior side thereof than it is at the posterior side thereof.

Note that the vertebrae support column 54 has a plurality of blood holes 60 extending through the lateral and anterior sides (and, although not shown in the figures, the posterior side) thereof (and thus through the mounting plate 56 as well). The blood holes 60 define a plurality of paths of fluid communication between the square aperture 58 extending through the vertebrae support column 54 and the exterior of the vertebrae support column 54 on the lateral, anterior, and posterior sides thereof.

Referring now particularly to FIG. 5, it may be seen that the mounting plate 56 consists of two 180 degree opposed L's having their respective bases mounted together, with their respective vertical legs extending in opposing directions from different ends of the common bases. The legs of the L's of the mounting plate 56 each have a pair of countersunk apertures 62 extending therethrough. The screws extending through the countersunk apertures 62 located in the leg of the L above the point of connection of the mounting plate 56 to the vertebrae support column 54 will be screwed into the upper vertebra, while the screws extending through the countersunk apertures 62 located in the leg of the L below the point of connection of the mounting plate 56 to the vertebrae support column 54 will be screwed into the lower vertebra.

Also located in the mounting plate 56 at its point of connection to the vertebrae support column 54 (the bases of the L's) are two countersunk angled apertures 64. One of the countersunk angled apertures 64 is oriented such that a screw (not illustrated in FIG. 5) inserted therethrough will engage an upper vertebra (not illustrated in FIG. 5), and the other of the countersunk angled apertures 64 is oriented such that another screw inserted therethrough will engage a lower vertebra (also not illustrated in FIG. 5).

Figure 11:
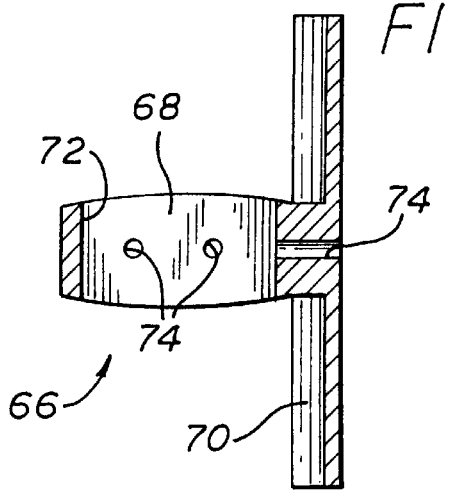
FIG. 11 is a cross-sectional view of the vertebral body T-cage illustrated in FIGS. 8 through 10.

Referring now to FIGS. 8 through 11, another alternate embodiment vertebral body T-cage 66 is illustrated which essentially consists of a vertebrae support column 68 having a curved mounting plate 70 attached to the side thereof. The side of the vertebrae support column 68 is attached to the curved mounting plate 70 at the midpoint of the curved mounting plate 70. The vertebrae support column 68 is square in cross-section, as illustrated in FIG. 10, and is hollow, having a square aperture 72 extending vertically therethrough. In addition, the lateral sides of the vertebrae support column 68 are convex curves on both the top and bottom of the vertebrae support column 68, as best illustrated in FIGS. 8 and 11.

Note that the vertebrae support column 68 has a plurality of blood holes 74 extending through the lateral and anterior sides (and, although not shown in the figures, the posterior side) thereof (and thus through the mounting plate 70 as well). The blood holes 74 define a plurality of paths of fluid communication between the square aperture 72 extending through the vertebrae support column 68 and the exterior of the vertebrae support column 68 on the lateral, anterior, and posterior sides thereof.

Referring now particularly to FIG. 9, a plurality of countersunk apertures 76 extend through the curved mounting plate 70 both above and below its point of connection to the vertebrae support column 68. The countersunk apertures 76 are arranged and configured to have mounting screws (not illustrated in FIG. 9) inserted therethrough to retain the vertebral body T-cage 66 in place intermediate two vertebrae (also not illustrated in FIG. 9). The screws extending through the countersunk apertures 76 located above the point of connection of the curved mounting plate 70 to the vertebrae support column 68 will be screwed into the upper vertebra, while the screws extending through the countersunk apertures 76 located below the point of connection of the curved mounting plate 70 to the vertebrae support column 68 will be screwed into the lower vertebra.

Also located in the curved mounting plate 70 at its point of connection to the vertebrae support column 68 are two countersunk angled apertures 78. One of the countersunk angled apertures 78 is oriented such that a screw (not illustrated in FIG. 9) inserted therethrough will engage an upper vertebra (not illustrated in FIG. 9), and the other of the countersunk angled apertures 78 is oriented such that another screw inserted therethrough will engage a lower vertebra (also not illustrated in FIG. 9).

Figure 12:
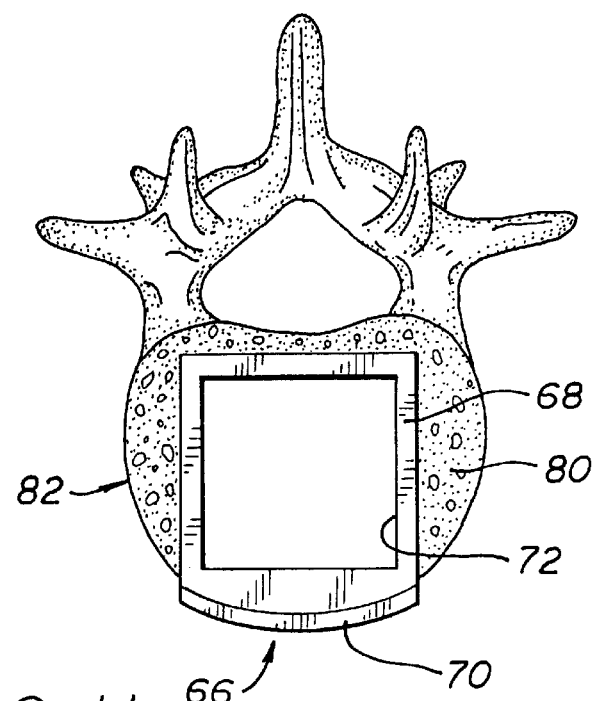
FIG. 12 is a top side (superior) plan view of the vertebral body T-cage illustrated in FIGS. 8 through 10 located on the superior endplate of a lower vertebra which is located immediately below a removed vertebra.
Figure 13:
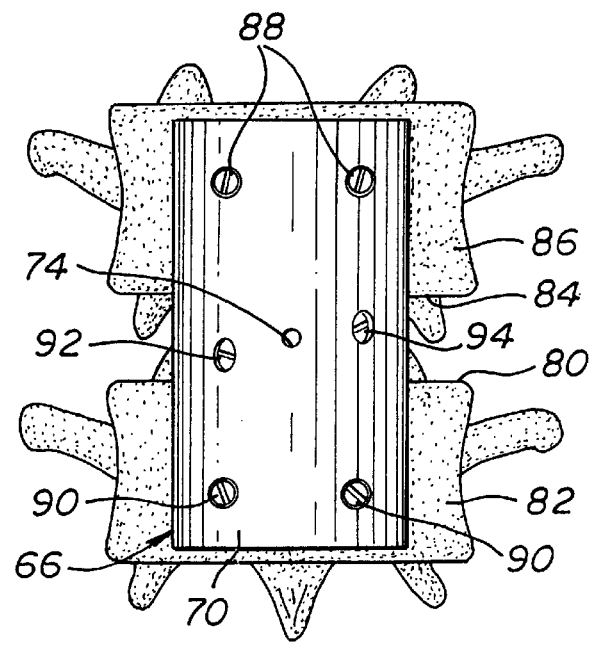
FIG. 13 is an anterior side view of the vertebral body T-cage illustrated in FIG. 12 installed between upper and lower vertebra respectively located immediately above and below a removed vertebra.
Figure 22:
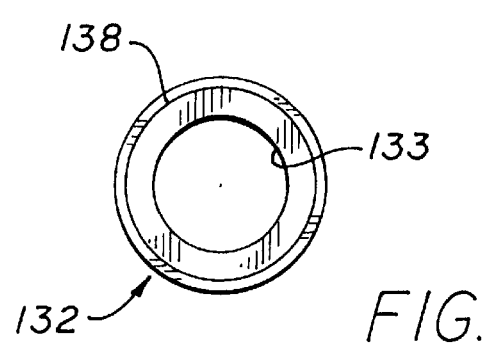
FIG. 22 is a top end view of the vertebrae support column of the vertebral body prosthesis illustrated in FIG. 19, showing the hollow interior thereof.
Figure 14:
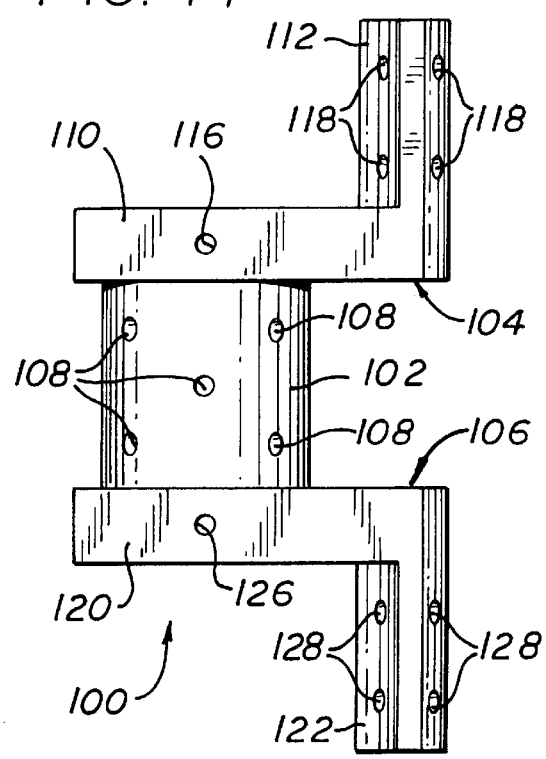
FIG. 14 is a side plan view of a fixed height vertebral body prosthesis constructed according to the teachings of the present invention for right side installation intermediate the endplates of vertebrae located immediately above and below a removed vertebra, showing a vertebrae support column having mounting brackets attached to the top and bottom thereof, and also showing a plurality of blood holes extending therethrough.
Figure 15:
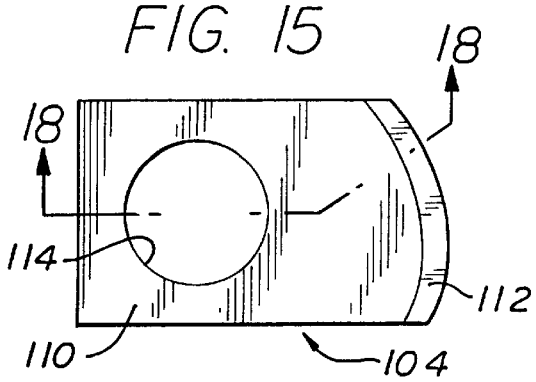
FIG. 15 is a top plan view of the mounting bracket mounted on the top of the vertebrae support column of the vertebral body prosthesis illustrated in FIG. 14, showing the configuration of a curved side mounting plate located thereon.
Figure 16:
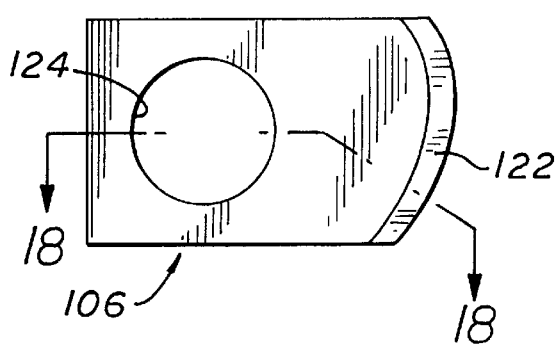
FIG. 16 is a bottom plan view of the mounting bracket mounted on the bottom of the vertebrae support column of the vertebral body prosthesis illustrated in FIG. 14, showing the configuration of a curved side mounting plate located thereon.

Referring next to FIGS. 12 and 13, the vertebral body T-cage 66 is illustrated as being installed intermediate a superior endplate 80 of a lower vertebra 82 and an inferior endplate 84 of an upper vertebra 86. The vertebral body T-cage 66 is installed following the removal of a vertebra (not illustrated) which was located intermediate the lower vertebra 82 and the upper vertebra 86. The vertebrae support column 68 of the vertebral body T-cage 66 is first packed with bone chips or marrow (not illustrated) and then is placed intermediate the superior endplate 80 of the lower vertebra 82 and the inferior endplate 84 of the upper vertebra 86.

A pair of screws 88 are inserted through the countersunk apertures 76 in the portion of the curved mounting plate 70 extending above the vertebrae support column 68 (illustrated in FIG. 9), and are screwed into the upper vertebra 86. Another pair of screws 90 are then inserted through the countersunk apertures 76 in the portion of the curved mounting plate 70 extending below the vertebrae support column 68 (also illustrated in FIG. 9), and are screwed into the lower vertebra 82. A screw 92 is inserted through the countersunk angled aperture 78 which is angled downwardly in the vertebral body T-cage 66, and is screwed into the lower vertebra 82. Finally, a screw 94 is inserted through the countersunk angled aperture 78 which is angled upwardly in the vertebral body T-cage 66, and is screwed into the upper vertebra 86.

Referring now to FIGS. 14 through 18, a fixed height vertebral body prosthesis 100 for installation intermediate the endplates of vertebrae (not illustrated in FIGS. 14 through 18) located immediately above and below a removed vertebra is illustrated. The fixed height vertebral body prosthesis 100 is for installation from the right side of the vertebrae, although it will at once be understood by those skilled in the art that the mirror image of the fixed height vertebral body prosthesis 100 could be used for installation from the left side of the vertebrae.

The fixed height vertebral body prosthesis 100 consists of a vertebrae support column 102 having an upper mounting bracket 104 mounted at the top thereof, and a lower mounting bracket 106 mounted at the bottom thereof. The vertebrae support column 102 is of cylindrical configuration, and is hollow. A plurality of blood holes 108 extend through the sides of the vertebrae support column 102, and define a plurality of paths of fluid communication between the interior and the exterior of the vertebrae support column 102.

Figure 18:
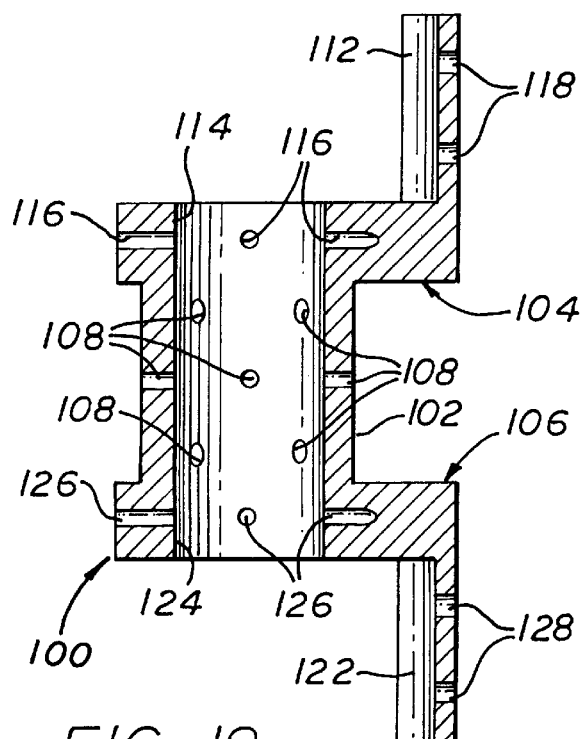
FIG. 18 is a cross-sectional view of the vertebral body prosthesis illustrated in FIGS. 14 through 17, showing the hollow interior of the vertebrae support column.

The upper mounting bracket 104 is illustrated to include a flat base member 110 having a curved mounting plate 112 mounted at one side thereof and extending upwardly therefrom. The base member 110 of the upper mounting bracket 104 has a circular aperture 114 extending vertically therethrough, which circular aperture 114 is in communication with the hollow interior of the vertebrae support column 102, as illustrated in FIG. 18. A plurality of blood holes 116 extend through the sides of the base member 110, and define a plurality of paths of fluid communication between the interior and the exterior of the base member 110.

Figure 17:
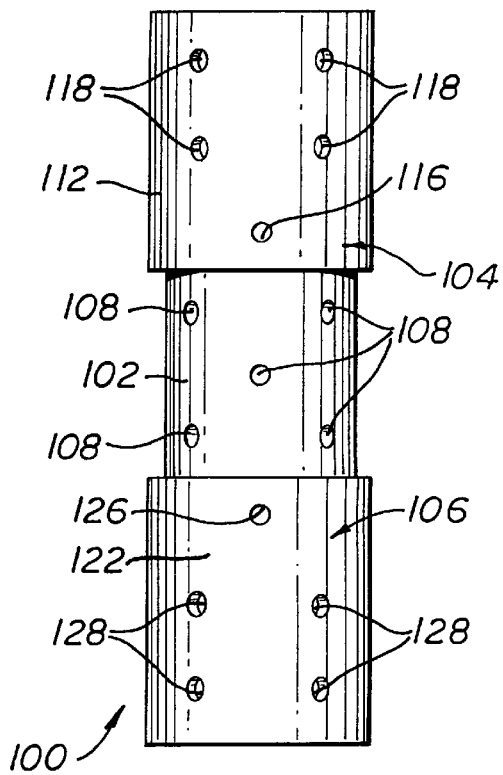
FIG. 17 is a back plan view of the vertebral body prosthesis illustrated in FIGS. 14 through 16, showing a plurality of apertures through which mounting screws may be inserted to retain the vertebral body prosthesis in place.

Referring now particularly to FIGS. 17 and 18, a plurality of apertures 118 extend through the curved mounting plate 112 above its point of connection to the base member 110. The apertures 118 are arranged and configured to have mounting screws (not illustrated in FIGS. 17 and 18) inserted therethrough to retain the upper mounting bracket 104 in place adjacent an upper vertebra (not illustrated in FIGS. 17 and 18) with the base member 110 under the endplate of the upper vertebra. The screws extending through the apertures 118 will be screwed into the upper vertebra to retain the upper mounting bracket 104 in place.

Referring again to FIGS. 14 through 18, the lower mounting bracket 106 is illustrated to include a flat base member 120 having a curved mounting plate 122 mounted at one side thereof and extending downwardly therefrom. The base member 120 of the lower mounting bracket 106 has a circular aperture 124 extending vertically therethrough, which circular aperture 124 is in communication with the hollow interior of the vertebrae support column 102, as illustrated in FIG. 18. A plurality of blood holes 126 extend through the sides of the base member 120, and define a plurality of paths of fluid communication between the interior and the exterior of the base member 120.

Referring now particularly to FIGS. 17 and 18, a plurality of apertures 128 extend through the curved mounting plate 122 below its point of connection to the base member 120. The apertures 128 are arranged and configured to have mounting screws (not illustrated in FIGS. 17 and 18) inserted therethrough to retain the lower mounting bracket 106 in place adjacent a lower vertebra (not illustrated in FIGS. 17 and 18) with the base member 120 on top of the endplate of the lower vertebra. The screws extending through the apertures 128 will be screwed into the lower vertebra to retain the lower mounting bracket 106 in place.

Referring now to FIGS. 19 through 23, a variable height vertebral body prosthesis 130 for installation intermediate the endplates of vertebrae (not illustrated in FIGS. 19 through 23) located immediately above and below a removed vertebra is illustrated. The variable height vertebral body prosthesis 130 is for installation from the right side of the vertebrae, although it will at once be understood by those skilled in the art that the mirror image of the variable height vertebral body prosthesis 130 could be used for installation from the left side of the vertebra.

The variable height vertebral body prosthesis 130 consists of three components which are assembled together. These three components are a vertebrae support column 132, an upper mounting bracket 134 for installation at the top of the vertebrae support column 132, and a lower mounting bracket 136 for installation at the bottom of the vertebrae support column 132. The vertebrae support column 132 is of essentially cylindrical configuration, and is hollow, having a circular aperture 133 extending therethrough. The top end of the vertebrae support column 132 has standard threads 138 located on the outside thereof. The bottom end of the vertebrae support column 132 has reverse threads 140 located on the outside thereof.

Located on the vertebrae support column 132 intermediate the standard threaded end 138 and the reverse threaded end 140 is a central portion which has a series of angularly spaced apertures 142 extending radially therethrough. The angularly spaced apertures 142 will be used to adjust the height of the variable height vertebral body prosthesis 130, as will become apparent below in conjunction with the discussion of FIGS. 24 and 25. A plurality of blood holes 144 extend through the sides of the vertebrae support column 132, and define a plurality of paths of fluid communication between the interior and the exterior of the vertebrae support column 132.

The upper mounting bracket 134 is illustrated to include a flat base member 146 mounted atop a cylindrical support 148. The base member 146 has a curved mounting plate 150 mounted at one side thereof and extending upwardly therefrom. The base member 146 and the cylindrical support 148 of the upper mounting bracket 134 have a standard threaded circular aperture 152 extending vertically therethrough, which standard threaded circular aperture 152 will receive the standard threaded end 138 of the vertebrae support column 132.

Thus, when the upper mounting bracket 134 is screwed onto the vertebrae support column 132, the standard threaded circular aperture 152 in the upper mounting bracket 134 is in communication with the circular aperture 133 extending through the vertebrae support column 132, as illustrated in FIG. 23. A plurality of blood holes 154 extend through the sides of the base member 146 and the cylindrical support 148, and define a plurality of paths of fluid communication relatively between the interiors and the exteriors thereof. Also located in the side of the cylindrical support 148 in a location which will be accessible during the installation of the variable height vertebral body prosthesis 130 is a threaded aperture 156.

Referring now particularly to FIGS. 19 and 23, a plurality of apertures 158 extend through the curved mounting plate 150 above its point of connection to the base member 146. The apertures 158 are arranged and configured to have mounting screws (not illustrated in FIGS. 19 and 23)

inserted therethrough to retain the upper mounting bracket 134 in place adjacent an upper vertebra (not illustrated in FIGS. 19 and 23) with the base member 146 under the endplate of the upper vertebra. The screws extending through the apertures 158 will be screwed into the upper vertebra to retain the upper mounting bracket 134 in place.

The lower mounting bracket 136 is illustrated to include a flat base member 160 mounted atop a cylindrical support 162. The base member 160 has a curved mounting plate 164 mounted at one side thereof and extending upwardly therefrom. The base member 160 and the cylindrical support 162 of the lower mounting bracket 136 have a reverse threaded circular aperture 166 extending vertically therethrough, which reverse threaded circular aperture 166 will receive the reverse threaded end 140 of the vertebrae support column 132.

Thus, when the lower mounting bracket 136 is screwed onto the vertebrae support column 132, the reverse threaded circular aperture 166 in the lower mounting bracket 136 is in communication with the circular aperture 133 extending through the vertebrae support column 132, as illustrated in FIG. 23. A plurality of blood holes 168 extend through the sides of the base member 160 and the cylindrical support 162, and define a plurality of paths of fluid communication relatively between the interiors and the exteriors thereof. Also located in the side of the cylindrical support 162 in a location which will be accessible during the installation of the variable height vertebral body prosthesis 130 is a threaded aperture 170.

Referring now particularly to FIGS. 19 and 23, a plurality of apertures 172 extend through the curved mounting plate 164 above its point of connection to the base member 160. The apertures 172 are arranged and configured to have mounting screws (not illustrated in FIGS. 19 and 23) inserted therethrough to retain the lower mounting bracket 136 in place adjacent a lower vertebra (not illustrated in FIGS. 19 and 23) with the base member 160 under the endplate of the lower vertebra. The screws extending through the apertures 172 will be screwed into the lower vertebra to retain the lower mounting bracket 136 in place.

Referring now to FIGS. 24 and 25, the variable height vertebral body prosthesis 130 is illustrated as being installed intermediate a superior endplate 174 of a lower vertebra 176 and an inferior endplate 178 of an upper vertebra 180. The variable height vertebral body prosthesis 130 is installed following the removal of a vertebra (not illustrated) which was located intermediate the lower vertebra 176 and the upper vertebra 180. The circular aperture 133 in the vertebrae support column 132, the standard threaded circular aperture 152 in the upper mounting bracket 134, and the reverse threaded circular aperture 166 in the lower mounting bracket 136 are first packed with bone chips or marrow (not illustrated). The variable height vertebral body prosthesis 130 is then placed intermediate the superior endplate 174 of the lower vertebra 176 and the inferior endplate 178 of the upper vertebra 180.

Four screws 182 are inserted through the apertures 158 in the curved mounting plate 150 of the upper mounting bracket 134 (illustrated in FIGS. 19 and 23), and are screwed into the upper vertebra 180. Four screws 184 are then inserted through the apertures 172 in the curved mounting plate 164 of the lower mounting bracket 136 (also illustrated in FIGS. 19 and 23), and are screwed into the lower vertebra 176.

A handle 186 is inserted into an opposed pair of the angularly spaced apertures 142 located at the midpoint of the vertebrae support column 132. The handle 186 is used to rotate the vertebrae support column 132 to adjust the height of the variable height vertebral body prosthesis 130. By rotating the vertebrae support column 132 in one direction, the upper mounting bracket 134 and the lower mounting bracket 136 will move further apart, thereby increasing the height of the variable height vertebral body prosthesis 130. By rotating the vertebrae support column 132 in the other direction, the upper mounting bracket 134 and the lower mounting bracket 136 will move closer together, thereby decreasing the height of the variable height vertebral body prosthesis 130.

Following the adjustment in height of the variable height vertebral body prosthesis 130 to the desired space, rotational movement of the vertebrae support column 132 with respect to the upper mounting bracket 134 and the lower mounting bracket 136 must be prevented. A setscrew 188 is screwed into the threaded aperture 156 in the cylindrical support 148 of the upper mounting bracket 134 (illustrated in FIG. 19) and into engagement with the standard threaded end 138 of the vertebrae support column 132. Similarly, a setscrew 190 is screwed into the threaded aperture 170 in the cylindrical support 162 of the lower mounting bracket 136 (illustrated in FIG. 19) and into engagement with the reverse threaded end 140 of the vertebrae support column 132.

Referring next to FIG. 26, an alternate embodiment upper mounting bracket 192 is illustrated which uses the same reference numerals as the upper mounting bracket 134 (illustrated in FIGS. 19, 20, and 23) for identical parts thereof. The upper mounting bracket 192 differs from the upper mounting bracket 134 only in that the upper mounting bracket 192 has a plurality of small spikes 194 extending from the superior side of the base member 146. The spikes 194 are for use to better retain the upper mounting bracket 192 in position against the inferior endplate 178 of the upper vertebra 180 (illustrated in FIG. 24).

Referring now to FIG. 27, another alternate embodiment component is illustrated, which is for use with either the upper mounting bracket 134 or the lower mounting bracket 136 (illustrated in FIGS. 19 through 23). A wedge-shaped spacer 196 is illustrated which is for use intermediate a mounting bracket (the upper mounting bracket 134 or the lower mounting bracket 136) and a vertebra endplate (the inferior endplate 178 of the upper vertebra 180 or the superior endplate 174 of the lower vertebra 176) to better fit the mounting bracket to the surface of the endplate of the vertebra.

The wedge-shaped spacer 196 consists of a rectangular, wedge-shaped member 198 having a circular aperture 200 extending vertically therethrough. The circular aperture 200 has a plurality of small spikes 202 extending from the superior side of the wedge-shaped member 198. The spikes 202 are optional, and act to better retain the wedge-shaped spacer 196 in position against a vertebra endplate (the inferior endplate 178 of the upper vertebra 180 or the superior endplate 174 of the lower vertebra 176).

Referring next to FIGS. 28 and 29, another alternate embodiment upper mounting bracket 204 is illustrated which uses the same reference numerals as the upper mounting bracket 134 (illustrated in FIGS. 19, 20, and 23) for identical parts thereof. The upper mounting bracket 204 differs from the upper mounting bracket 134 only in that the upper mounting bracket 204 has an annular recess 206 located in the top surface of the base member 146 around the standard threaded circular aperture 152. The depth of the annular recess 206 is illustrated in FIG. 29.

Referring to FIGS. 30 and 31, a rotatable wedge spacer 208 is illustrated which consists of a short cylindrical base 210 having a cylindrical segment of a wedge 212 mounted thereupon. A centrally-located circular aperture 214 extends vertically through both the cylindrical wedge 212 and the cylindrical base 210, as illustrated in FIG. 31. The rotatable wedge spacer 208 is for installation on the upper mounting bracket 204 illustrated in FIGS. 28 and 29.

Referring now to FIGS. 28 through 31, it may be seen that the height of the cylindrical base 210 of the rotatable wedge spacer 208 is of a size to fit within the annular recess 206 located in the top surface of the base member 146 of the upper mounting bracket 204. With the rotatable wedge spacer 208 thus installed in place on the upper mounting bracket 204, only the cylindrical wedge 212 of the rotatable wedge spacer 208 will extend above the surface of the base member 146. By rotating the rotatable wedge spacer 208, the cylindrical wedge 212 can accommodate different uneven surface configurations on the endplate of a vertebra (not illustrated in FIGS. 28 through 31) on which the upper mounting bracket 204 is to be mounted.

Referring next to FIG. 32, a convex member 216 is illustrated which consists of a spherical segment 218 having a flat top surface (e.g., a minority portion of a sphere which has been cut off by a plane). The spherical segment 218 of the convex member 216 has a centrally-located circular aperture 220 extending therethrough.

Referring now to FIGS. 33 and 34, yet another alternate embodiment upper mounting bracket 222 is illustrated which uses the same reference numerals as the upper mounting bracket 134 (illustrated in FIGS. 19, 20, and 23) for identical parts thereof. The upper mounting bracket 222 differs from the upper mounting bracket 134 only in that the upper mounting bracket 222 has a concave recess 224 located in the top surface of the base member 146 around the standard threaded circular aperture 152. The depth of the concave recess 224 is illustrated in FIG. 34.

Referring now to FIGS. 32 through 34, the spherical segment 218 of the convex member 216 is arranged and configured to fit partially within the concave recess 224 in the base member 146 of the upper mounting bracket 222. Since the spherical segment 218 of the convex member 216 is free to move within the concave recess 224 in the base member 146 of the upper mounting bracket 222, it will be appreciated by those skilled in the art that the portion of the spherical segment 218 of the convex member 216 which is located above the surface of the base member 146 of the upper mounting bracket 222 will act as a wedge, moving to accommodate different uneven surface configurations on the endplate of a vertebra (not illustrated in FIGS. 32 through 34) on which the upper mounting bracket 22 is to be mounted.

It may therefore be appreciated from the above detailed description of the preferred embodiment of the present invention that it teaches an improved vertebral body prosthesis which may be used following the removal of the anterior column of a vertebra to reestablish spinal stability and maintain proper spacing between the vertebrae located immediately above and below the removed vertebra. The vertebral body prosthesis of the present invention is of a design and physical configuration which may be easily installed in place intermediate the endplates of the two adjacent vertebrae via a posterior surgical approach. The implant procedure for the vertebral body prosthesis of the present invention also does not require the use of complex tools to install and position the vertebral body prosthesis intermediate the two vertebrae.

The vertebral body prosthesis of the present invention is implantable in a surgical procedure featuring both reduced implant trauma to the patient and reduced time required for the surgeon to implant the device. When the vertebral body prosthesis of the present invention is installed in place intermediate the vertebrae located immediately above and below the removed vertebra, it will securely and permanently maintain the integrity and security of the spinal column. The vertebral body prosthesis of the present invention promotes prompt and permanent ingrowth of bone material intermediate the vertebrae located immediately above and below the removed vertebra to facilitate permanent fusion of the spinal segment. The vertebral body prosthesis of the present invention is made of biocompatible material compatible with long term implant in the human body, and it may be either adjustable in length or made in different sizes and configurations to fit a wide variety of patients and different locations in the spine.

The vertebral body prosthesis of the present invention is of a construction which is both durable and long lasting, and it requires no maintenance once it is implanted. The vertebral body prosthesis of the present invention is also of a simple mechanical design and relatively inexpensive construction to enhance its market appeal and thereby afford it the broadest possible market. Finally, all of the aforesaid advantages and objectives of the vertebral body prosthesis of the present invention are achieved without incurring any substantial relative disadvantage.

Although an exemplary embodiment of the vertebral body prosthesis of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A vertebral body prosthesis for installation intermediate the inferior endplate of an upper vertebra and the superior endplate of a lower vertebra to replace a removed vertebra, said vertebral body prosthesis comprising:

a vertebrae support member having an upper end and a lower end, said upper end of said vertebrae support member being arranged and configured for placement adjacent to the inferior endplate of the upper vertebra, said lower end of said vertebrae support member being arranged and configured for placement adjacent to the superior endplate of the lower vertebra, said vertebrae support member having a channel located therein which channel is open at said upper and lower ends of said vertebrae support member;

an upper mounting plate mechanically connected to said upper end of said vertebrae support member at a side thereof, said upper mounting plate extending upwardly from said upper end of said vertebrae support member, said upper mounting plate having a horizontally concave contour to lie close adjacent to a side of the upper vertebra when said upper end of said vertebrae support member is located close adjacent to the inferior endplate of the upper vertebra, said upper mounting plate having a plurality of angularly spaced-apart mounting apertures located therein such that screws inserted therethrough will extend into the side of the upper vertebra at a converging relative angle to each other to secure said upper end of said vertebrae support member in a fixed position with respect to the upper vertebra; and a lower mounting plate mechanically connected to said lower end of said vertebrae support member at a side thereof, said lower mounting plate extending downwardly from said lower end of said vertebrae support member, said lower mounting plate having a horizontally concave contour to lie close adjacent to a side of the lower vertebra when said lower end of said vertebrae support member is located close adjacent to the superior endplate of the lower vertebra, said lower mounting plate having a plurality of angularly spaced-apart mounting apertures located therein such that screws inserted therethrough will extend into the side of the lower vertebra at a converging relative angle to each other to secure said lower end of said vertebrae support member in a fixed position with respect to the lower vertebra.

2. A vertebral body prosthesis as defined in claim 1, wherein said vertebrae support member has a plurality of blood holes extending through the sides thereof, said blood holes thereby defining a plurality of paths of fluid communication between said channel located in said vertebrae support member and the exterior of said vertebrae support member.

3. A vertebral body prosthesis as defined in claim 1, wherein said vertebrae support member comprises:
    a hollow column of square cross-section, said hollow column having upper and lower ends and having a square aperture extending vertically therethrough intermediate said upper and lower ends of said column.

4. A vertebral body prosthesis as defined in claim 3, wherein said upper and lower ends of said hollow column are essentially flat.

5. A vertebral body prosthesis as defined in claim 3, wherein said upper and lower ends of said hollow column comprise convex curved surfaces on opposing lateral sides of said hollow column.

6. A vertebral body prosthesis as defined in claim 3, wherein said upper and lower ends of said hollow column are spaced further apart on one side of said hollow column than they are on an opposing side of said hollow column.

7. A vertebral body prosthesis as defined in claim 1, wherein said upper and lower mounting plates are arranged and configured for placement adjacent the anterior sides of the upper and lower vertebrae, respectively.

8. A vertebral body prosthesis as defined in claim 1, wherein said vertebrae support member comprises:
    a hollow vertebrae support column having an upper end and a lower end thereof;
    an upper base member for installation onto said upper end of said vertebrae support column, said upper base member having an aperture extending therethrough which aperture is in communication with the hollow interior of said vertebrae support column, said upper mounting plate being mounted onto a side of said upper base member; and
    a lower base member for installation onto said lower end of said vertebrae support column, said lower base member having an aperture extending therethrough which aperture is in communication with the hollow interior of said vertebrae support column, said lower mounting plate being mounted onto a side of said lower base member.

9. A vertebral body prosthesis as defined in claim 8, wherein said upper and lower base members are permanently and fixedly installed on said upper and lower ends of said vertebrae support column, said vertebral body prosthesis thereby being of a fixed height.

10. A vertebral body prosthesis as defined in claim 8, wherein said upper and lower base members are movably installed on said upper and lower ends of said vertebrae support column such that said upper and lower base members may be moved closer together or further away relative to each other, said vertebral body prosthesis thereby being of an adjustable height.

11. A vertebral body prosthesis as defined in claim 8, wherein said vertebrae support column comprises:
    a threaded outer surface located at said upper end of said vertebrae support column; and
    a threaded outer surface located at said lower end of said vertebrae support column; and wherein said upper base member comprises:
    a threaded inner surface located in said aperture extending through said upper base member, said threaded outer surface located at said upper end of said vertebrae support column being screwed into said threaded inner surface located in said aperture extending through said upper base member; and wherein said lower base member comprises:
    a threaded inner surface located in said aperture extending through said lower base member, said threaded outer surface located at said lower end of said vertebrae support column being screwed into said threaded inner surface located in said aperture extending through said lower base member.

12. A vertebral body prosthesis as defined in claim 11, wherein said threaded outer surface located at said upper end of said vertebrae support column and said threaded inner surface located in said aperture extending through said upper base member have threads in a first direction, and wherein said threaded outer surface located at said lower end of said vertebrae support column and said threaded inner surface located in said aperture extending through said lower base member have threads in a second direction opposite to said first direction.

13. A vertebral body prosthesis as defined in claim 12, wherein said threaded outer surface located at said upper end of said vertebrae support column and said threaded inner surface located in said aperture extending through said upper base member have standard (right hand) threads, and wherein said threaded outer surface located at said lower end of said vertebrae support column and said threaded inner surface located in said aperture extending through said lower base member have reverse (left hand) threads.

14. A vertebral body prosthesis as defined in claim 12, wherein said vertebrae support column additionally comprises:
    a central portion having a series of angularly spaced apertures extending radially therethrough, wherein a handle may be inserted into an opposed pair of said angularly spaced apertures to rotate said vertebrae support column to adjust the height of said vertebral body prosthesis.

15. A vertebral body prosthesis as defined in claim 12, additionally comprising:
    an upper setscrew for adjustable installation in said upper base member to selectively secure said upper end of said vertebrae support column in a fixed position in said threaded inner surface located in said aperture extending through said upper base member; and
    a lower setscrew for adjustable installation in said lower base member to selectively secure said lower end of said vertebrae support column in a fixed position in said threaded inner surface located in said aperture extending through said lower base member.

16. A vertebral body prosthesis as defined in claim 1, wherein said upper and lower mounting plates are arranged and configured for placement adjacent either the right or the left lateral sides of the upper and lower vertebrae, respectively.

17. A vertebral body prosthesis as defined in claim 1, wherein said vertebral body prosthesis is made of titanium.

18. A vertebral body prosthesis as defined in claim 1, additionally comprising:
- a first plurality of small spikes extending from the superior side of said upper base member; and
- a second plurality of small spikes extending from the inferior side of said lower base member.

19. A vertebral body prosthesis as defined in claim 1, additionally comprising:
- a wedge-shaped member for installation intermediate at least one of said upper and lower base members and said upper and lower vertebrae, respectively.

20. A vertebral body prosthesis as defined in claim 1, additionally comprising:
- a recess located in at least one of said upper and lower base members; and
- a wedging member having a first portion receivable in said recess and a second portion extending above said recess and defining a movable wedge.

21. A vertebral body prosthesis for installation intermediate the inferior endplate of an upper vertebra and the superior endplate of a lower vertebra to replace a removed vertebra, said vertebral body prosthesis comprising:
- a vertebrae support column having an upper standard threaded end and a lower reverse threaded end thereof, said vertebrae support column having a channel located therein which channel is open at said upper and lower ends of said vertebrae support column;
- an upper base member for installation onto said upper standard threaded end of said vertebrae support column, said upper base member having a standard threaded aperture extending therethrough which aperture is in communication with said channel in said vertebrae support column, said upper base member being arranged and configured for placement adjacent to the inferior endplate of the upper vertebra;
- an upper mounting plate mechanically connected to said upper base member at a side thereof, said upper mounting plate extending upwardly from said upper base member, said upper mounting plate having a horizontally concave contour to lie close adjacent to a side of the upper vertebra when said upper base member is located close adjacent to the inferior endplate of the upper vertebra, said upper mounting plate having a plurality of angularly spaced-apart mounting apertures located therein such that screws inserted therethrough will extend into the side of the upper vertebra at a converging relative angle to each other to secure said upper end of said vertebrae support member in a fixed position with respect to the upper vertebra;
- a lower base member for installation onto said lower reverse threaded end of said vertebrae support column, said lower base member having a reverse threaded aperture extending therethrough which aperture is in communication with said channel in said vertebrae support column, said lower base member being arranged and configured for placement adjacent to the superior endplate of the lower vertebra; and
- a lower mounting plate mechanically connected to said lower base member at a side thereof, said lower mounting plate extending downwardly from said lower base member, said lower mounting plate having a horizontally concave contour to lie close adjacent to a side of the lower vertebra when said lower base member is located close adjacent to the superior endplate of the lower vertebra, said lower mounting plate having a plurality of angularly spaced-apart mounting apertures located therein such that screws inserted therethrough will extend into the side of the lower vertebra at a converging relative angle to each other to secure said lower end of said vertebrae support member in a fixed position with respect to the lower vertebra.

22. A vertebral body prosthesis for installation intermediate the inferior endplate of an upper vertebra and the superior endplate of a lower vertebra to replace a removed vertebra, said vertebral body prosthesis comprising:
- a vertebrae support member having an upper end and a lower end, said upper end of said vertebrae support member being arranged and configured for placement adjacent the inferior endplate of the upper vertebra, said lower end of said vertebrae support member being arranged and configured for placement adjacent the superior endplate of the lower vertebra, said vertebrae support member being hollow intermediate said upper and lower ends thereof;
- an upwardly extending upper mounting plate mechanically connected to said upper end of said vertebrae support member at a side thereof, said upper mounting plate having a horizontally concave contour, said upper mounting plate having a plurality of angularly spaced-apart mounting apertures located therein such that screws inserted therethrough will extend into the side of the upper vertebra at a converging relative angle to each other; and
- a downwardly extending lower mounting plate mechanically connected to said lower end of said vertebrae support member at a side thereof, said lower mounting plate having a horizontally concave contour, said lower mounting plate having a plurality of angularly spaced-apart mounting apertures located therein such that screws inserted therethrough will extend into the side of the upper vertebra at a converging relative angle to each other.

23. A method of making a vertebral body prosthesis for installation intermediate the inferior endplate of an upper vertebra and the superior endplate of a lower vertebra to replace a removed vertebra, said method comprising:
- providing a vertebrae support member having an upper end and a lower end, said upper end of said vertebrae support member being arranged and configured for placement adjacent to the inferior endplate of the upper vertebra, said lower end of said vertebrae support member being arranged and configured for placement adjacent to the superior endplate of the lower vertebra;
- defining a channel in said vertebrae support member, said channel being open at said upper and lower ends of said vertebrae support member;
- mechanically connecting an upper mounting plate to said upper end of said vertebrae support member at a side thereof, said upper mounting plate extending upwardly from said upper end of said vertebrae support member, said upper mounting plate having a horizontally concave contour to lie close adjacent to a side of the upper vertebra when said upper end of said vertebrae support member is located close adjacent to the inferior endplate of the upper vertebra, said upper mounting plate having a plurality of angularly spaced-apart mounting apertures located therein such that screws inserted therethrough will extend into the side of the upper vertebra at a converging relative angle to each other to secure said upper end of said vertebrae support member in a fixed position with respect to the upper vertebra; and mechanically connecting a lower mounting plate to said lower end of said vertebrae support member at a side thereof, said lower mounting plate extending downwardly from said lower end of said vertebrae support member, said lower mounting plate having a horizontally concave contour to lie close adjacent to a side of the lower vertebra when said lower end of said vertebrae support member is located close adjacent to the superior endplate of the lower vertebra, said lower mounting plate having a plurality of angularly spaced-apart mounting apertures located therein such that screws inserted therethrough will extend into the side of the lower vertebra at a converging relative angle to each other to secure said lower end of said vertebrae support member in a fixed position with respect to the lower vertebra.

\* \* \* \* \*